(12) United States Patent
Deeley et al.

(10) Patent No.: US 8,552,216 B2
(45) Date of Patent: *Oct. 8, 2013

(54) PROCESS FOR THE CARBONYLATION OF DIMETHYL ETHER

(75) Inventors: Jon Michael Stewart Deeley, York (GB); Evert Jan Ditzel, Goole (GB); David John Law, Beverley (GB); Mark Stephen Roberts, Beverley (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 640 days.

This patent is subject to a terminal disclaimer.

(21) Appl. No.: 12/451,058

(22) PCT Filed: Apr. 23, 2008

(86) PCT No.: PCT/GB2008/001414
§ 371 (c)(1),
(2), (4) Date: Oct. 23, 2009

(87) PCT Pub. No.: WO2008/132438
PCT Pub. Date: Nov. 6, 2008

(65) Prior Publication Data
US 2010/0121099 A1     May 13, 2010

(30) Foreign Application Priority Data

Apr. 26, 2007   (EP) ..................... 07251760

(51) Int. Cl.
*C07C 67/37* (2006.01)

(52) U.S. Cl.
USPC ......................... 560/240; 560/232

(58) Field of Classification Search
USPC ................. 560/232, 240; 568/885, 902
See application file for complete search history.

(56) References Cited

U.S. PATENT DOCUMENTS

| 5,218,140 | A | * | 6/1993 | Wegman | 560/232 |
| 5,286,900 | A | * | 2/1994 | Hansen et al. | 560/232 |
| 6,127,432 | A | * | 10/2000 | Wegman et al. | 518/715 |
| 6,521,783 | B1 | * | 2/2003 | Wegman et al. | 560/232 |
| 7,309,798 | B2 | * | 12/2007 | Cheung et al. | 560/232 |
| 7,465,822 | B2 | * | 12/2008 | Cheung et al. | 560/232 |
| 7,491,842 | B2 | * | 2/2009 | Smith | 560/232 |
| 7,642,372 | B2 | * | 1/2010 | Smith | 560/232 |
| 7,842,833 | B2 | * | 11/2010 | Ellis | 560/232 |
| 2006/0287551 | A1 | * | 12/2006 | Cheung et al. | 560/232 |

FOREIGN PATENT DOCUMENTS

WO   2006/121778   11/2006

OTHER PUBLICATIONS

International Search Report for PCT/GB2008/001414, mailed Aug. 20, 2008.
Written Opinion of the International Searching Authority for PCT/GB2008/001414, mailed Aug. 20, 2008.
Cheung et al., "Site Requirements and Elementary Steps in Dimethyl Ether Carbonylation Catalyzed by Acidic Zeolites", Journal of Catalysis, Volume Date 2007, 14 pages. XP002453503.

\* cited by examiner

*Primary Examiner* — Johann R Richter
*Assistant Examiner* — Pancham Bakshi
(74) *Attorney, Agent, or Firm* — Nixon & Vanderhye

(57) ABSTRACT

Process for the production of methyl acetate by carbonylating a dimethyl ether feed with carbon monoxide under substantially anhydrous conditions, in the presence of a zeolite catalyst effective for the carbonylation. The carbonylation is carried out at a temperature in the range of 275 to 350° C. and in the presence of hydrogen.

14 Claims, 4 Drawing Sheets

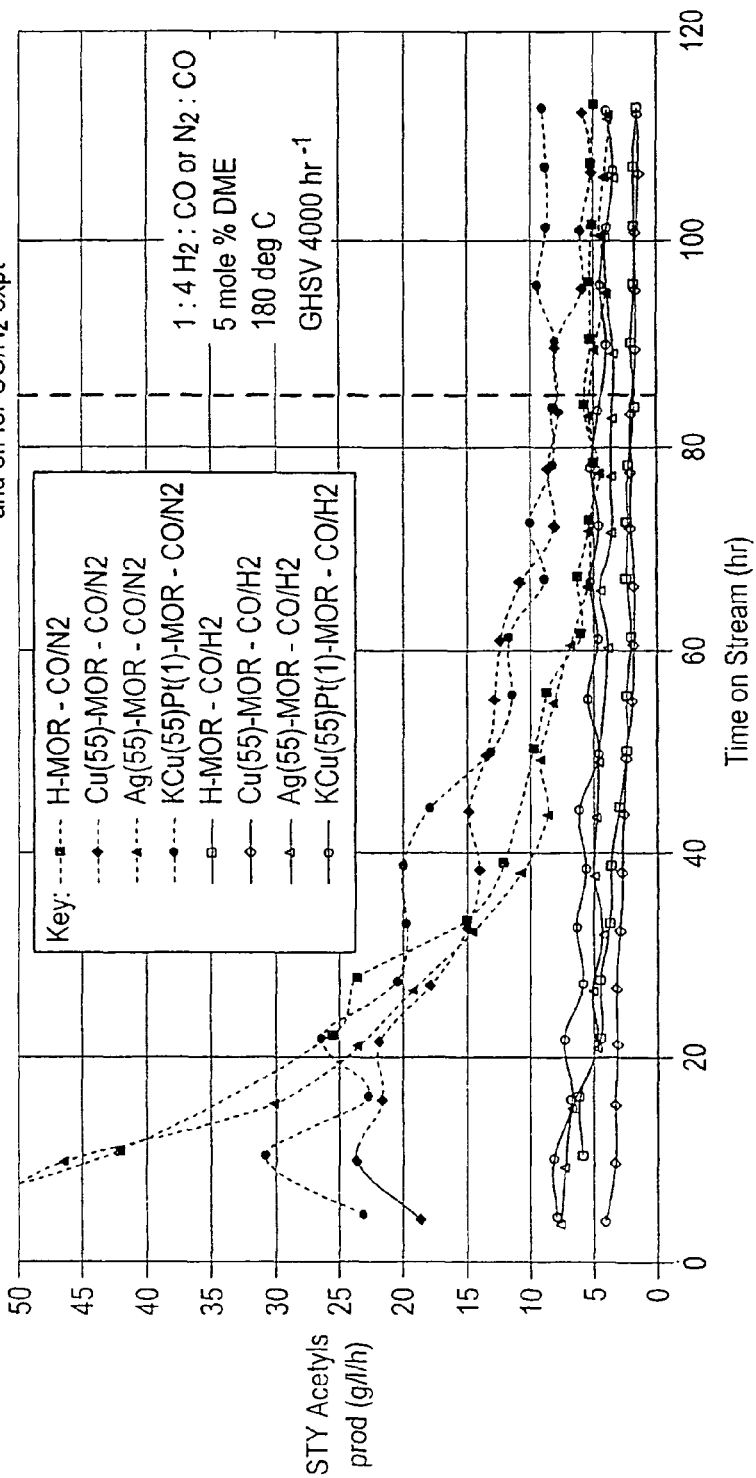

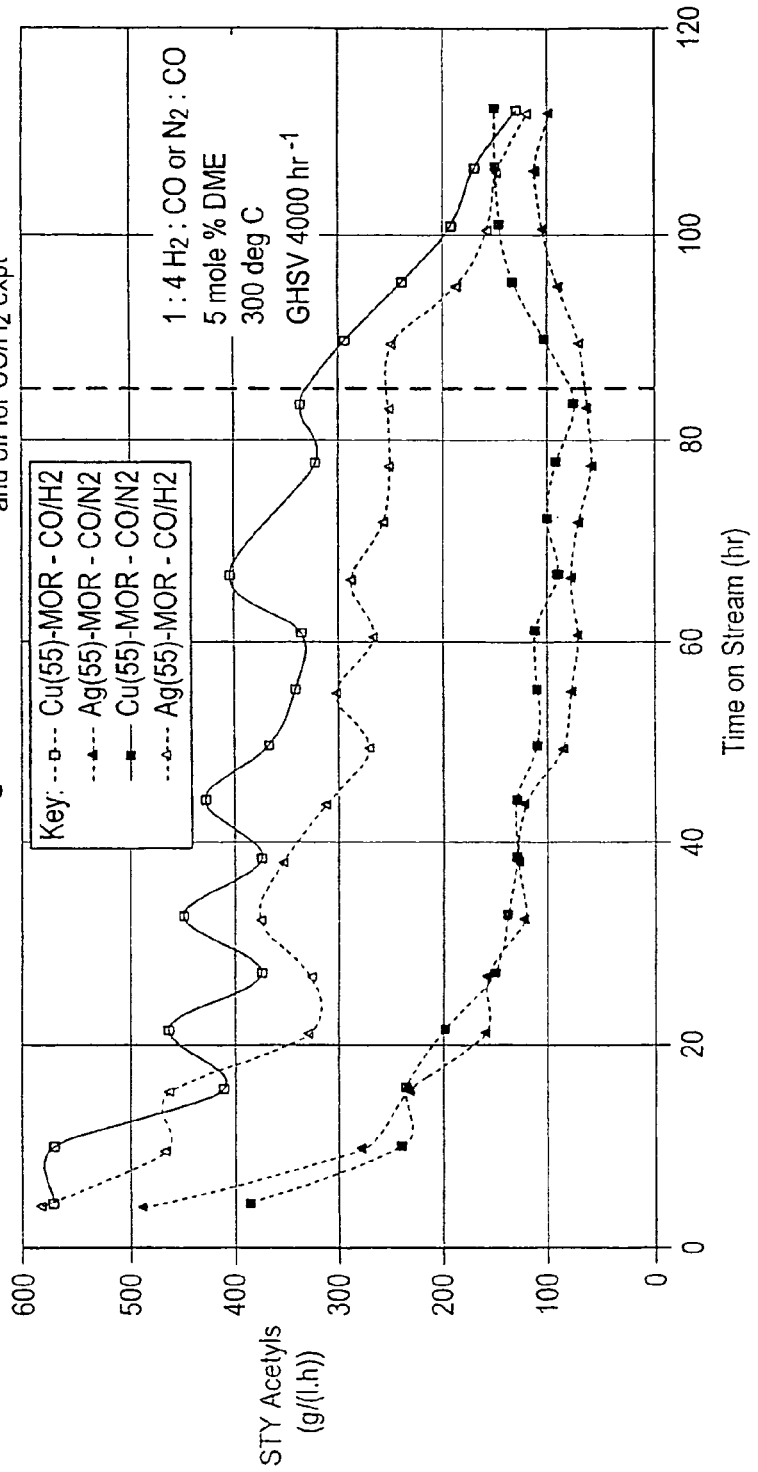
Fig. 3  Effect of Hydrogen at 300 deg C

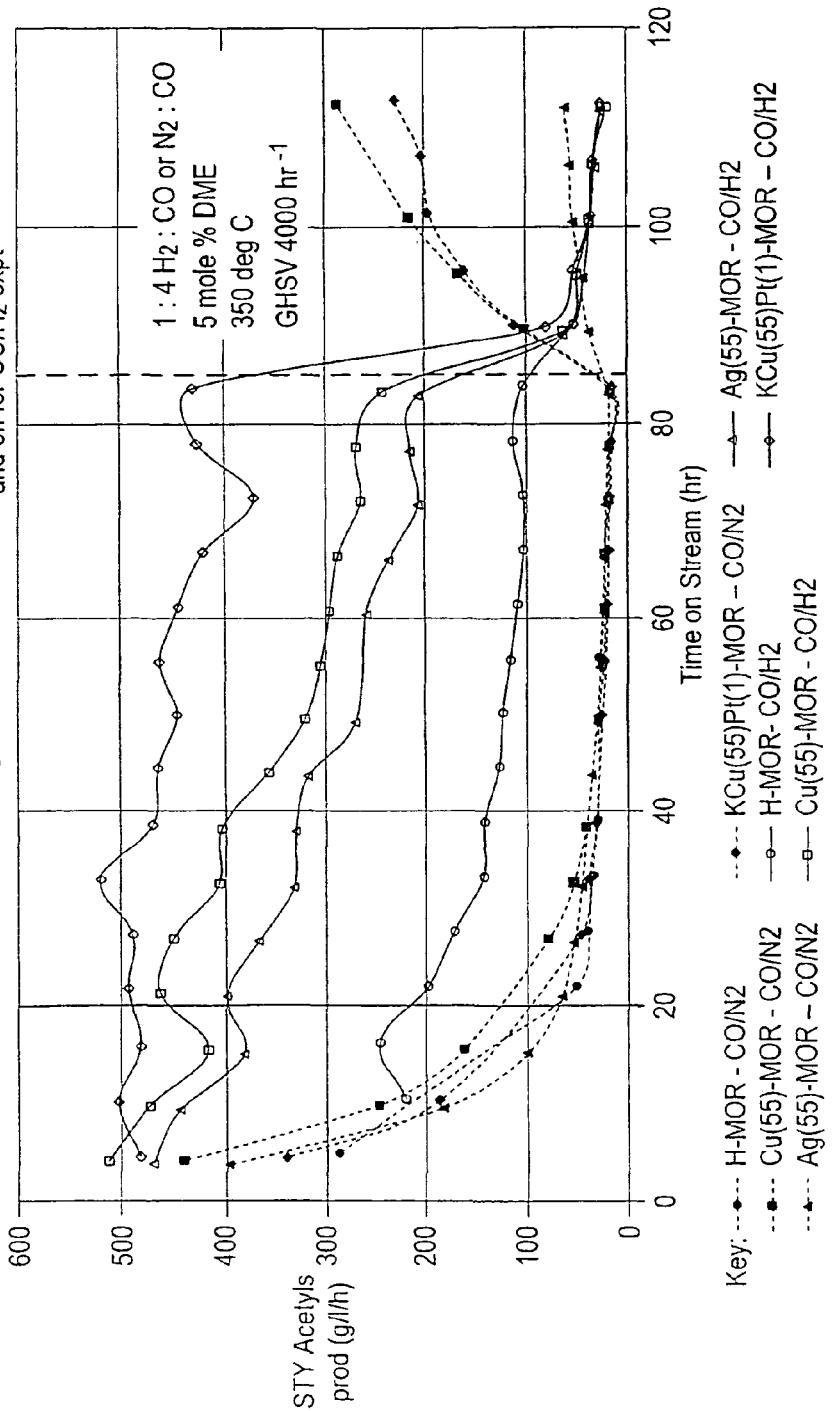

PROCESS FOR THE CARBONYLATION OF DIMETHYL ETHER

This application is the U.S. national phase of International Application No. PCT/GB2008/001414, filed 23 Apr. 2008, which designated the U.S. and claims priority to European Application No. 07251760.0, filed 26 Apr. 2007, the entire contents of each of which are hereby incorporated by reference.

This invention relates to a process for preparing methyl acetate by reacting dimethyl ether with carbon monoxide in the presence of a zeolite catalyst.

Methyl acetate is used industrially in petrochemical processes, particularly as a feed for the production of acetic acid and/or acetic anhydride.

The commercial production of acetic acid is operated as a homogeneous liquid-phase process in which the carbonylation reaction is catalysed by a Group VIII noble metal such as rhodium or iridium and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous gas phase process using an iodide free solid catalyst could be developed.

EP-A-0 596 632 describes a vapour phase process for the carbonylation of methanol to produce acetic acid in the presence of a modified mordenite catalyst at high temperatures and pressures.

WO 01/07393 describes a process for the catalytic conversion of a feedstock comprising carbon monoxide and hydrogen to produce at least one of an alcohol; ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof. However, the use of zeolites to catalyse the carbonylation reaction is not exemplified.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of a modified mordenite catalyst at a temperature in the range 250-600° C. and a pressure in the range 10 to 200 bar. The use of dimethyl ether as a feedstock is not exemplified.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst. According to this patent application, the carbonylation process is run at temperatures at or below 250° C., and preferably from about 150 to about 180° C. to minimise by-product formation.

In view of the above-mentioned prior art, there remains the need for a heterogeneous gas phase process for the production of methyl acetate from dimethyl ether under substantially anhydrous conditions using a zeolite catalyst which is superior to the other processes using carbonylatable reactants as a feed.

It has now been found that if the carbonylation process is carried out at a temperature in the range 240° C. to 350° C. and in the presence of hydrogen then improved productivity and/or catalyst stability may be achieved. The impact of hydrogen on productivity and/or catalyst stability in the range 240° C. to 350° C. can be further enhanced by the presence of one or more promoter metals on the zeolite.

Accordingly, the present invention provides a process for the production of methyl acetate which process comprises the carbonylation of a dimethyl ether feed with carbon monoxide under substantially anhydrous conditions, in the presence of a zeolite catalyst effective for said carbonylation, wherein said carbonylation is carried out at a temperature in the range of 240° C. to 350° C. and in the presence of hydrogen.

The present invention solves the problem defined above by operating the process at high temperature and in the presence of hydrogen to give good productivities to methyl acetate product. The finding that this can be achieved using hydrogen at high temperatures is surprising because from the work described in WO 2006/121778 mentioned above, it would be expected that the presence of hydrogen would have no or very little effect on the formation rate of methyl acetate in a zeolite catalysed dimethyl ether carbonylation process.

The dimethyl ether used as the feed in the process of the present invention may be substantially pure dimethyl ether. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. In the process of the present invention the dimethyl ether feed may comprise small amounts of methanol provided that the amount of methanol present in the feed is not so great as to inhibit the carbonylation of dimethyl ether to methyl acetate product. It has been found that 5 wt % or less, such as 1 wt % or less of methanol may be tolerated in the dimethyl ether feed.

Suitably, dimethyl ether is present in the feed at a concentration in the range 0.1 to 20 mol %, such as 1.5 mol % to 20 mol % or 1.5 mol % to 10 mol %, for example 1.5 mol % to 5 mol %, based on the total feed (including recycles).

The carbon monoxide may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

The process of the present invention is carried out in the presence of hydrogen. The hydrogen may be fed as a separate stream to the carbonylation reactor or it may be fed in combination with, for example carbon monoxide. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1, for example, 1:1 to 4:1.

The molar ratio of carbon monoxide to dimethyl ether is suitably in the range 1:1 to 99:1, such as 2:1 to 60:1.

The zeolite catalyst may be any zeolite which is effective to catalyse the carbonylation of dimethyl ether with carbon monoxide to produce methyl acetate.

Zeolites are available from commercial sources, generally in the Na, $NH_4$ form or H-form of the zeolite. The $NH_4$ form can be converted to the acid (H-form) by known techniques, such as calcination at high temperature. The Na form can be converted to the acid (H-form) by converting first to an $NH_4$ form by ion exchange with ammonium salts such as ammonium nitrate. Alternatively, zeolites may be synthesised using known techniques.

Zeolites comprise a system of channels which may be interconnected with other channel systems or cavities such as side-pockets or cages. The ring structures are generally 12-member rings, 10-member rings or 8 member rings. A zeolite may possess rings of different sizes. The zeolites for use in the present invention preferably contain at least one channel which is defined by an 8-member ring. Most preferably, the 8-member ring channel is interconnected with at least one channel defined by a ring with 10 and/or 12 members. The window size of the channel systems should be such that the reactant dimethyl ether and carbon monoxide molecules can diffuse freely in and out of the zeolite framework. Suitably, the window size of an 8-member ring channel may be at least 2.5×3.6 Angstroms. The *Atlas of Zeolite Framework Types* (C. Baerlocher, W. M. Meier, D. H. Olson, $5^{th}$ ed. Elsevier, Amsterdam, 2001) in conjunction with the web-based version (http://www.iza-structure.org/databases/) is a compendium of topological and structural details about zeolite frameworks, including the types of ring structures present in a zeolite and the dimensions of the channels defined by each ring type. Examples of zeolites suitable for use in the present invention include zeolites of framework type MOR, for example mordenite, FER, such as ferrierite, OFF, for example, offretite and GME, for example gmelinite.

For the process of the present invention it is preferred that the zeolite has a silica to alumina ratio of at least 5 but preferably less than or equal to 100, such as in the range 7 to 40, for example 10 to 30. Where the aluminium atoms have been replaced by framework modifier elements such as gallium, it is preferred that the ratio of silica:$X_2O_3$ where X is a trivalent element, such as aluminium; gallium, iron and/or boron, is at least 5 and preferably less than or equal to 100, such as in the range 7 to 40, for example 10 to 30.

Preferably, the zeolite for use in the present invention is loaded with one or more metals such as copper, silver, nickel, iridium, rhodium, platinum, palladium or cobalt and mixtures thereof.

In one embodiment of the present invention the zeolite catalyst is a mordenite zeolite. The mordenite may be employed in the acid form (H-mordenite) or it may be optionally ion-exchanged or otherwise loaded with one or more metals such as copper, silver, nickel, iridium, rhodium, platinum, palladium or cobalt.

The metal loading on a zeolite, for example, mordenite may be expressed in terms of the fractional loading of the metal as gram atoms of metal per gram atom of aluminium in the mordenite. The metal loading can also be expressed as a mole percentage loading relative to aluminium in the mordenite through the relationship:

mol % Metal=(gram atoms Metal/gram atoms aluminium)×100

Thus, for example, a loading of 0.55 gram atoms of copper per aluminium in the mordenite equates to a 55 mol % loading of copper relative to aluminium in the mordenite.

Suitably, the metal loading may be in the range of 1 to 200 mol % relative to aluminium, for example, 40 to 120 mol %, 50 to 120 mol %, such as 50 to 110 mol % or 55 to 120 mol %, such as 55 to 110 mol %.

The mordenite framework, may in addition to the silicon and aluminium atoms, contain additional trivalent elements, such as boron, gallium and/or iron.

Where the mordenite contains at least one or more trivalent framework, the metal loading in the mordenite can be expressed in terms of the fractional loading of the metal as gram atoms of metal per gram atom of total trivalent elements in the mordenite. The metal loading can also be expressed as a mole percentage loading relative to total trivalent elements in the mordenite through the relationship:

mol % Metal=(gram atoms Metal/gram atoms of total trivalent elements)×100

Because the carbonylation reaction is to be conducted substantially in the absence of water, it is preferred that the zeolite catalyst is dried prior to use. The zeolite may be dried, for example by heating to a temperature of 400 to 500° C.

It is preferred that the zeolite catalyst is activated immediately before use by heating the zeolite at elevated temperature for at least one hour under flowing nitrogen, carbon monoxide, hydrogen or mixtures thereof.

The process is carried out under substantially anhydrous conditions, i.e in the substantial absence of water. The carbonylation of dimethyl ether to methyl acetate does not generate water in-situ. Water has been found to inhibit the carbonylation of dimethyl ether to form methyl acetate. Thus, in the process of the present invention, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate. Suitably, the dimethyl ether may contain, 2.5 wt % or less, such as 2.4 wt % or less, for example, 0.5 wt % or less of water.

The process of the present invention is carried out at a temperature in the range of 240° C. to 350° C. Suitably, the temperature may be in the range 250 to 350° C., such as 275 to 350° C., for example, 275 to 325° C.

The process of the present invention may be carried out at a total pressure in the range 1 to 100 barg. Suitably, the pressure may be in the range of 10 barg to 100 barg, such as 10 to 80 barg, for example, 30 to 80 barg or 30 barg to 100 barg.

The hydrogen partial pressure is suitably in the range 0.1 to 50 barg, such as 3 to 30 barg, for example 5 to 25 barg.

The carbon monoxide partial pressure should be sufficient to permit the production of methyl acetate product but is suitably in the range 0.1 to 50 barg.

The Gas Hourly Space Velocity (GHSV) is suitably in the range 500 to 40,000 $h^{-1}$, such as 2000 to 20,000 $h^{-1}$.

The process of the present invention is suitably carried out by passing dimethyl ether vapour, hydrogen gas and carbon monoxide gas through a fixed or fluidised bed of the zeolite catalyst maintained at the required temperature.

Preferably, the process of the present invention is carried out substantially in the absence of halides, such as iodide. By the term 'substantially' is meant that the halide, for example, iodide content of the reactant gases (dimethyl ether and carbon dioxide) and catalyst is less than 500 ppm, preferably less than 100 ppm.

The primary product of the process is methyl acetate but small amounts of acetic acid may also be produced. The methyl acetate produced by the process of the present invention can be removed in the form of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

The process may be operated as either a continuous or a batch process, preferably as a continuous process.

The invention is now illustrated with reference to the following Examples.

EXAMPLE 1

This Example demonstrates the effect of the addition of hydrogen on the carbonylation of dimethyl ether at 180 to 300° C.

Catalyst Preparation

Catalyst A—H-Mordenite

Mordenite with a silica to alumina ratio of 20 (ex Süd-Chemie) was compacted with the powtec roller compactor at 250 bar using a total of 4 cycles, then crushed and sieved to a particle size fraction of 125 to 160 microns. 2.5 g of the mordenite was impregnated with 2250 μL deionised water. After the impregnation the mordenite was left at ambient conditions on a shaker for 1 hour. After the shaking the mordenite was transferred to a forced convection oven (air as atmosphere) heated to 80° C. for 20 hours. After the drying step the mordenite was calcined in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The mordenite was then cooled down to room temperature in the muffle oven under (dry) air flow 1 L/min.

The mordenite was then gently pushed through a 160 μm sieve and sieved to obtain particles having a size in the range 125-160 μm.

Catalyst B—Ag Loaded Mordenite

Mordenite with a silica to alumina ratio of 20 (ex Süd-Chemie) was compacted with the powtec roller compactor at 250 bar using a total of 4 cycles, then crushed and sieved to a particle size fraction of 125 to 160 microns. The compacted mordenite was treated with a silver (I) nitrate solution, to obtain 55 mol % of silver relative to aluminium. The LOI (loss on ignition, 600° C.) of the mordenite was measured (typically 10-20%, in this case 18.0%) to account for the amount of water adsorbed on the mordenite in order to determine the amount of metal solution required to achieve the desired platinum loading. A solution of 426 μL silver (I) nitrate of concentration of 4 mol/L dissolved in 1824 μL deionised $H_2O$ was made-up and used to impregnate 2.5 g of the mordenite. After the impregnation the mordenite was left at ambient conditions on a shaker for 1 hour. After the shaking the silver loaded mordenite was transferred to a forced convection oven (air as atmosphere) heated to 80° C. for 20 hours. After the drying step the silver loaded mordenite was calcined in air in a muffle oven (oven-volume=12 L) at a temperature of 500° C. under air (air flow 1 L/min) at a ramp rate of 1° C./min to a temperature of 120° C., held at 120° C. for 180 minutes, then the temperature was increased by 1° C./min to 500° C., held at 500° C. for 180 minutes. The silver loaded mordenite was then cooled down to room temperature in the muffle oven under (dry) air flow 1 L/min. The silver loaded mordenite was then gently pushed through a 160 μm sieve and sieved to obtain particles having a size in the range 125-160 μm.

Carbonylation of Dimethyl Ether

Dimethyl ether was carbonylated with carbon monoxide in the presence of each of the Catalysts A and B and in the presence of hydrogen. The experiments were carried out in a pressure flow reactor unit consisting of 16 identical reactors of the type described in for example, WO 2005063372. Prior to the loading of the catalyst into the reactor, a 5 cm (approx.) bed of steatite of sieve fraction of 100-350 μm was placed in the respective catalyst holder. A 5 cm (approx.) zone of corundum of sieve fraction of 125-160 μm was placed on top of the steatit bed. 1.0 ml of catalyst was placed on top of the corundum bed. The catalyst was covered by approximately 5 cm corundum bed of a particle size of 125-160 μm. A 5 cm (approx.) zone of steatite of sieve fraction of 100-350 μm was placed on top of the corundum bed. Every zone was concreted via hitting or vibrating to get a stable bed and a defined starting height of the catalyst zone. The catalyst was then pressurised to 30 bar with $N_2$ at a flow rate of 4 L/h. The catalyst was then heated at 0.5 deg. C./min to a holding temperature of 220° C., where it was held for a dwell time of 3 hours. Subsequently the temperature was ramped to 400° C. at 0.5 deg. C./min, again followed by a dwell time of 3 hours. At this point catalyst activation was considered complete and the reactor temperature was decreased to 180° C. After the temperature have reached the 180° C. the gas feed was switched to a mixture of carbon monoxide, nitrogen and dimethyl ether (DME) with a $CO/N_2/DME$ ratio of 78/20/2 at a flow rate of 4 l/h. Dimethyl ether was fed at 0.08 l/h as a vapour, to obtain a $CO/N_2/DME$ ratio in the total feed of 78/20/2 on a molar basis. In addition, $N_2$ was introduced at a variable rate of 0-50 ml/min to equalise the pressure swings between the 16 reactor exits. The exit stream from the reactor was passed to a gas chromatograph to determine the concentration of reactants and carbonylation products. The reaction was allowed to continue for 24 hours under conditions of 180° C., 30 bar, a gas hourly space velocity (GHSV) of 4000/h and a $CO/N_2/DME$ ratio of 78/20/2 on a molar basis. After 24 hrs total reaction time the $CO/N_2/DME$ feed was switched to $CO/H_2/DME$. The reaction was allowed to continue for a further 24 hours under conditions of 180° C., 30 bar, a gas hourly space velocity (GHSV) of 4000/h with a $CO/H_2/DME$ molar ratio of 78/20/2. After 48 hrs total reaction time the temperature was increased from 180° C. to 240° C. The reaction was allowed to continue for a further 12 hours under conditions of 240° C., 30 bar, a gas hourly space velocity. (GHSV) of 4000/h with a $CO/H_2/DME$ molar ratio of 78/20/2. After 61 hrs total reaction time the temperature was increased from 240° C. to 300° C. The reaction was allowed to continue for a further 23 hours under conditions of 300° C., 30 bar, a gas hourly space velocity (GHSV) 4000/h with a $CO/H_2/DME$ molar ratio of 78/20/2. The results of the carbonylation experiments for each of the catalysts are shown in FIG. 1.

BRIEF DESCRIPTION OF DRAWINGS

The invention will now be described in more detail with reference to the accompanying drawings in which.

FIG. 2 is a plot of STY acetyls product versus time on stream for the effect of hydrogen at 180° C.;

FIG. 3 is a plot of STY acetyls versus time on stream for the effect of hydrogen at 300° C.; and FIG. 4 is a plot of STY acetyls versus time on stream for the effect of hydrogen at 350° C.

FIG. 1 illustrates the effect on the rate of formation of methyl acetate product by the addition of hydrogen to the carbonylation reaction. The results shown in FIG. 1 demonstrate that the presence of hydrogen has no/little effect on the carbonylation reaction at lower temperatures (180° C.) but it does have an impact at higher temperatures (240° C. and above).

EXAMPLES 2 AND 3

Figure 1:
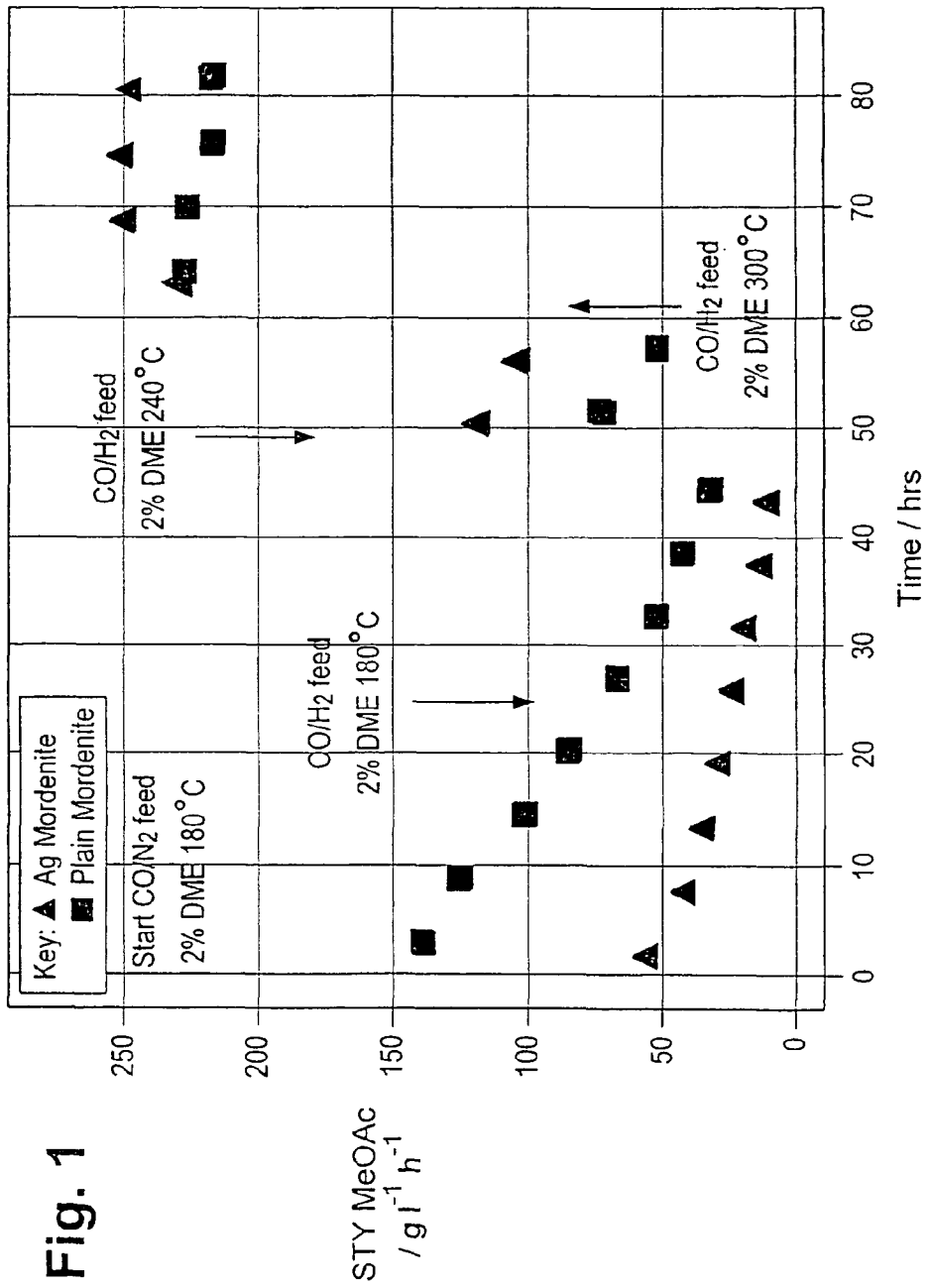
FIG. 1 illustrates the affect on the rate of formation on methyl acetate product by the addition of hydrogen to the carbonylation reaction.

These Examples demonstrate the effect of hydrogen on the carbonylation of dimethyl ether at temperatures in the range 180 to 350° C. by (i) carrying out the carbonylation initially in the presence of hydrogen and then in the absence of hydrogen and (ii) carrying out the carbonylation initially in the absence of hydrogen and then in the presence of hydrogen.

Catalyst Preparation

Catalyst C—H-Mordenite
H-Mordenite (H-MOR) with a silica to alumina ratio of 20 (ex Süd-Chemie) was calcined in a muffle oven (oven volume=18 L) under a static atmosphere of air using the following temperature programme. The temperature was increased from room temperature to 90° C. at a ramp rate of 3° C./min and held at this temperature for 2 hours. The temperature was then increased from 90° C. to 110° C. at a ramp rate of 1° C./min and held at this temperature for 2 hours. The temperature was then increased from 110° C. to 500° C. with a ramp rate of 5° C./min and held at this temperature for 6 hours before being allowed to cool to room temperature. The mordenite was then compacted at 12 tonnes in a 33 mm die set using a Specac Press, and then crushed and sieved to a particle size fraction of 212 to 335 microns.
Catalyst D—Cu-Mordenite—Cu(55)-MOR
H-mordenite (80 g) with a silica to alumina ratio of 20 (ex Süd-Chemie) was weighed into a 500 mL round bottomed flask together with 14.29 g of copper (II) nitrate hemipentahydrate (98% ACS) and a stirrer bar. Sufficient deionised water (ca. 100 mL) was then added to the flask to obtain a thick slurry. The top of the flask was then covered loosely and the flask left to stir overnight. The copper loaded mordenite was then dried under reduced vacuum using a rotary evaporator before being dried in an oven at 90° C. for 12 hours. The mordenite was then calcined in a muffle oven (oven volume=18 L) under a static atmosphere of air using the following temperature programme. The temperature was increased from room temperature to 90° C. at a ramp rate of 3° C./min and held at this temperature for 2 hours. The temperature was then increased from 90° C. to 110° C. at a ramp rate of 1° C./min and held at this temperature for 2 hours. The temperature was then increased from 110° C. to 500° C. with a ramp rate of 5° C./min and held at this temperature for 6 hours before being allowed to cool to room temperature. The copper loaded mordenite was then compacted at 12 tonnes in a 33 mm die set using a Specac Press, and crushed and sieved to a particle size fraction of 212 to 335 microns. The mordenite had a copper loading of ca. 55 mole % relative to aluminium contained in the mordenite.
Catalyst E—Ag-Mordenite—Ag(55)-MOR
Catalyst E was prepared in the same way as Catalyst D except that silver nitrate (99+% ACS) (10.47 g for 80 g mordenite) was used instead of copper (II) nitrate hemipentahydrate (98% ACS). The resulting mordenite had a silver loading of ca. 55 mole % relative to aluminium.
Catalyst F—CuPt-Mordenite—KCu(55)Pt(1)-MOR
Catalyst F was prepared according to the method used in the preparation of Catalyst D except that 0.20 g of potassium tetranitroplatinate (ex Aldrich) was used instead of copper (II) nitrate and Catalyst D itself was used as the zeolite substrate instead of H-mordenite. The resulting mordenite had a copper loading of 55 mole % and a platinum loading of 1 mole % relative to aluminium contained in the mordenite.

EXAMPLE 2

Carbonylation of Dimethyl Ether in the Initial Presence of Hydrogen

Dimethyl ether was carbonylated in the presence of each of Catalysts C to F at a range of temperatures 180-350° C. and at a pressure of 70 bang. The experiments were carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Only blocks 1 to 3 were used in this Example. Into each tube 50 micro liters of catalyst (designed to give a GHSV of 4000 h$^{-1}$) was loaded onto a metal sinter having a pore size of 20 micrometers. The catalysts were heated at a ramp rate of 5° C./min. to 100° C. under 98.6 mole % $N_2$ and 1.4 mole % He at atmospheric pressure at a flow rate of 3.4 ml/min, and held at this temperature for 1 hour. The reactor was then pressurised to 70 barg and the system held at this condition for 1 hour. The gas feed was then changed to 63.1 mole % carbon monoxide, 15.8 mole % hydrogen, 19.7 mole % nitrogen and 1.4 mole % He at a gas flow rate of 3.4 ml/min, and the system was heated at a ramp rate of 3° C./min. to a temperature of 300° C. The system was then held at this condition for 3 hours. After this, the temperature of blocks 1 to 3 was adjusted to 180, 300, and 350° C. respectively, and the system was allowed to stabilise for 10 minutes. At this point catalyst activation was considered complete, and the gas feed was changed to 63.1 mole % carbon monoxide, 15.8 mole % hydrogen, 14.8 mole % nitrogen, 1.4 mole % helium and 4.9 mole % dimethyl ether at a gas flow rate of 3.4 ml/min. The reaction was allowed to continue for ca. 85 hours under these conditions before the gas feed was changed to 63.1 mole % carbon monoxide, 30.6 mole % nitrogen, 1.4 mole % helium and 4.9 mole % dimethyl ether at a gas flow rate of 3.4 ml/min. These conditions were maintained for ca. 28 hours. The exit stream from the reactor was passed to two gas chromatographs; a Varian 4900 micro GC with three columns (Molecular sieve 5A, Porapak® Q, and CP-Wax-52) each equipped with a thermal conductivity detector and an Interscience Trace GC with two columns (CP-Sil 5 and CP-Wax 52) each equipped with a flame ionisation detector. The results of Example 2 are shown in FIGS. 2 to 4. FIGS. 2 to 4 illustrate the effect of hydrogen at 180° C., 300° C. and 350° C. respectively. In the Figures, productivity, $STY_{acetyls}$ is as defined the STY for the production of AcOH plus the STY for the production of MeOAc multiplied by $MW_{AcOH}/MW_{MeOAc}$.

EXAMPLE 3

Carbonylation of Dimethyl Ether in the Initial Absence of Hydrogen

Dimethyl ether was carbonylated in the presence of each of Catalysts C to F, at a range of temperatures 180-350° C. and at a pressure of 70 barg in accordance with the experimental procedure described in Example 2 above, except that after the system had been held for 3 hours at a temperature of 300° C., the temperature of blocks 1 to 3 was adjusted to 180, 300, and 350° C. respectively, the gas feed was changed to 63.1 mole % carbon monoxide, 35.5 mole % nitrogen and 1.4 mole % helium, and the system was allowed to stabilise for 10 minutes. At this point catalyst activation was considered complete, and the gas feed was changed to 63.1 mole % carbon monoxide, 30.6 mole % nitrogen, 1.4 mole % helium and 4.9 mole % dimethyl ether at a gas flow rate of 3.4 ml/min. The reaction was allowed to continue for ca. 85 hours under these conditions before the gas feed was changed to 63.1 mole % carbon monoxide, 15.8 mole % hydrogen, 14.8 mole % nitrogen, 1.4 mole % helium and 4.9 mole % dimethyl ether at a gas flow rate of 3.4 ml/hour. These conditions were then maintained for ca. 28 hours. The results of Example 3 are shown in FIGS. 2 to 4.

FIG. 2 corroborates the teaching of the prior art, that is, the presence of hydrogen at low temperatures has little/no effect on productivity. However, as FIGS. 3 and 4 clearly illustrate, at higher temperatures, the presence of hydrogen in the carbonylation of dimethyl ether provides an improvement in productivity. From FIG. 4 it can be seen that hydrogen has a greater effect on productivity when the zeolite catalyst is loaded with a metal.

EXAMPLES 4 TO 9

These examples illustrate the effect of carrying out the carbonylation of dimethyl ether at varying hydrogen partial pressures.

Catalyst Preparation

Catalyst G—Cu-Mordenite—Cu(55)-MOR

Catalyst G was prepared in the same way as Catalyst D except that 17.8 g of copper nitrate hemipentahydrate (98% ACS, ex Aldrich) instead of 14.29 g was used to load 100 g of H-mordenite with a silica to alumina ratio of 20 (ex Süd-Chemie) and the resulting copper loaded mordenite was calcined for 16 hours at 500° C.

Catalyst H—Ag-Mordenite—Ag(42)-MOR

Catalyst H was prepared in the same way as Catalyst E except that 5.06 g silver nitrate (99+% ACS, ex Aldrich) instead of 10.47 g was used to load 50.6 g H-mordenite with a silica to alumina ratio of 20 (ex Süd-Chemie) and the resulting silver loaded mordenite was calcined for 16 hours at 500° C.

Catalyst I—H-Mordenite

H-mordenite with a silica to alumina ratio of 20 (ex Süd-Chemie) was compacted at 12 tonnes in a 33 mm die set using a Specac Press, and then crushed and sieved to a particle size fraction of 212 to 335 microns.

Catalyst D, Catalyst E and Catalyst C were used in Examples 4, 6 and 8 respectively except that prior to use each catalyst was sieved to a particle size of 500 to 1000 microns after calcining. Catalyst G, Catalyst H and Catalyst I were used in Examples 5, 7 and 9 respectively.

EXAMPLE 4

Carbonylation of Dimethyl Ether

A stainless steel reactor tube was packed with 2.0 ml of Catalyst D and topped with 1 ml glass beads. The reactor tube was mounted in the downstream leg of a stainless steel U-tube. The upstream leg of the U-tube was packed with glass beads. The catalyst, in the reactor/U-tube, was heated from ambient temperature to 100° C. at a ramp rate of 3° C./min under helium gas at a pressure of 46.7 barg and a flow rate of 125 ml/min NTP (20 C 1 atm) and maintained at this condition for 18 h. The catalyst was then heated from 100° C. to 300° C. at a ramp rate of 3° C./min under a mixture of carbon monoxide, hydrogen and helium (carbon monoxide 48.4 vol %, hydrogen 48.4 vol %, He 3.2 vol %) at a pressure of 46.7 barg and a flow rate of 202 ml/min NTP (20° C., 1 atm) and maintained at this condition for 2 hours. Dimethyl ether (BOC, >99.99%) was then fed to the reactor as a liquid from a high pressure syringe pump onto the glass beads in the upstream leg of the U-tube where it was vapourised and mixed with the gas feed before passing over the catalyst. The liquid dimethyl ether was fed at a rate of 0.0185 mL/min with the syringe barrel cooled to 5° C. The reactor pressure was controlled by a pressure control valve downstream of the reactor and the temperature of the reactor effluent gas was maintained at at least 150° C. The reactor effluent gas was let down to atmospheric pressure across the pressure control valve. The effluent gas was cooled to 60° C. and passed through a knock out pot to trap any relatively involatile materials before the effluent stream was passed to a mass spectrometer and gas chromatograph for analysis. From the gas chromatography analysis of the reactor effluent for methyl acetate and acetic acid the space time yield (STY) of acetyls products was calculated as the molar equivalent weight of acetic acid corresponding to the sum of the methyl acetate and acetic acid produced expressed as grams of acetic acid per hour per liter of catalyst.

EXAMPLES 5 TO 9

Example 4 was repeated using each of Catalysts G, E, H, C and I. The flow rates (expressed as volume of gas at NTP) of dimethyl ether, carbon monoxide, helium and hydrogen and the total pressure used in each example are given in Table 1. The calculated partial pressures of the feed components and the space time yield (STY) of acetyls products are also shown in Table 1.

TABLE 1

| | Example | | | | | |
|---|---|---|---|---|---|---|
| | 4 | 5 | 6 | 7 | 8 | 9 |
| Catalyst | Cat D Cu(55)-MOR | Cat G Cu(55)-MOR | Cat E Ag(55)-MOR | Cat H Ag(42)-MOR | Cat C H-MOR | Cat I H-MOR |
| He NTP ml min$^{-1}$ | 6.7 | 6.7 | 6.7 | 6.7 | 6.7 | 6.7 |
| H$_2$ NTP ml min$^{-1}$ | 97.3 | 24.0 | 97.3 | 24.0 | 97.3 | 24.0 |
| CO NTP ml min$^{-1}$ | 97.3 | 97.3 | 97.3 | 97.3 | 97.3 | 97.3 |
| DME NTP ml min$^{-1}$ | 6.7 | 6.7 | 6.7 | 6.7 | 6.7 | 6.7 |
| GHSV h$^{-1}$ | 6050 | 4000 | 6050 | 4000 | 6050 | 4000 |
| Inlet pressure barg | 46.7 | 30.0 | 46.7 | 30.0 | 46.7 | 30.0 |
| Partial pressure He barg | 1.6 | 1.6 | 1.6 | 1.6 | 1.6 | 1.6 |

TABLE 1-continued

|  | Example | | | | | |
| --- | --- | --- | --- | --- | --- | --- |
|  | 4 | 5 | 6 | 7 | 8 | 9 |
| Partial pressure $H_2$ barg | 22.3 | 5.6 | 22.3 | 5.6 | 22.3 | 5.6 |
| Partial pressure CO barg | 22.3 | 22.6 | 22.3 | 22.6 | 22.3 | 22.6 |
| Partial pressure DME barg | 1.6 | 1.6 | 1.6 | 1.6 | 1.6 | 1.6 |
| Temperature ° C. | 300 | 300 | 300 | 300 | 300 | 300 |
| STY (AcOH eq g $l^{-1}$ $h^{-1}$) 20 h | 481 | 303 | 437 | 134 | 141 | 49 |
| STY (AcOH eq g $l^{-1}$ $h^{-1}$) 40 h |  |  |  | 117 |  | 41 |
| STY (AcOH eq g $l^{-1}$ $h^{-1}$) 110 h | 358 | 163 | 298 |  | 76 |  |
| STY (AcOH eq g $l^{-1}$ $h^{-1}$) 210 h | 304 | 110 | 241 |  | 62 |  |

From a comparison of Examples 4 and 5 it can be seen that increasing the hydrogen partial pressure results in a substantial increase in product STY. Furthermore, increasing the hydrogen partial pressure results in a decrease in the rate of loss of catalytic activity. In Example 4 (at the higher hydrogen partial pressure), the catalytic activity after 210 hours on stream is 63% of the catalytic activity after 20 hours, but in Example 5 (with the lower hydrogen partial pressure) the catalytic activity after 210 hours on stream was only 36% of the activity after 20 hours. Similar effects are seen by comparing the results of Example 6 with Example 7 and the results of Example 8 with Example 9.

The invention claimed is:

1. A process for the production of methyl acetate which process comprises the carbonylation of a dimethyl ether feed with carbon monoxide under substantially anhydrous conditions, in the presence of a zeolite catalyst effective for said carbonylation, wherein said carbonylation is carried out at a temperature in the range of 275 to 350° C. and in the presence of hydrogen.

2. A process according to claim 1 wherein the molar ratio of carbon monoxide:hydrogen is in the range 1:3 to 15:1.

3. A process according to claim 1 wherein the process is carried out at a hydrogen partial pressure in the range 0.1 to 50 barg.

4. A process according to claim 3 wherein the process is carried out at a hydrogen partial pressure in the range 5 to 25 barg.

5. A process according to claim 1 wherein the process is carried out at a total pressure in the range 10 to 100 barg.

6. A process according to claim 5 wherein the process is carried out at a total pressure in the range 30 to 80 barg.

7. A process according to claim 1 wherein the zeolite is loaded with one or more metals.

8. A process according to claim 1 wherein the zeolite contains at least one channel which is defined by an 8-member ring.

9. A process according to claim 8 wherein the zeolite is selected from the group consisting of mordenite, ferrierite, offretite and gmelinite.

10. A process according to claim 9 wherein the mordenite is H-mordenite or is ion-exchanged or otherwise loaded with at least one metal selected from the group consisting of copper, nickel, iridium, silver, rhodium, platinum, palladium and cobalt.

11. A process according to claim 10 wherein the metal is present in the mordenite at a loading in the range 50 to 120 mol % relative to aluminum.

12. A process according to claim 1 wherein at least some of the methyl acetate product is hydrolyzed to acetic acid.

13. A process according to claim 1 wherein the carbonylation is carried out in the presence of a mordenite zeolite at a temperature in the range of 275° C. to 350° C., at a total pressure in the range 30 to 80 barg and a carbon monoxide:hydrogen molar ratio of 1:1 to 4:1.

14. A process according to claim 1 wherein the carbonylation is carried out in the presence of a mordenite zeolite at a temperature in the range of 275° C. to 350° C., at a total pressure in the range 30 to 80 barg and a hydrogen partial pressure in the range 5 to 25 barg.

* * * * *